United States Patent [19]

Knaup

[11] Patent Number: 5,227,540
[45] Date of Patent: Jul. 13, 1993

[54] PROCESS FOR THE PREPARATION OF PRIMARY AND SECONDARY FLUORINE-CONTAINING ALCOHOLS

[75] Inventor: Wolfgang Knaup, Burgkirchen, Fed. Rep. of Germany

[73] Assignee: Hoechst Aktiengesellschaft, Frankfurt am Main, Fed. Rep. of Germany

[21] Appl. No.: 919,310

[22] Filed: Jul. 24, 1992

[30] Foreign Application Priority Data

Jul. 26, 1991 [DE] Fed. Rep. of Germany ....... 4124807

[51] Int. Cl.$^5$ .................. C07C 31/38; C07C 31/40
[52] U.S. Cl. .................. 568/842; 568/812; 568/841
[58] Field of Search .......... 568/841, 842, 812

[56] References Cited

U.S. PATENT DOCUMENTS

| | | | |
|---|---|---|---|
| 3,022,356 | 2/1962 | Ver Nooy, III | 568/842 |
| 3,532,659 | 10/1970 | Hager et al. | 568/842 |
| 4,346,250 | 8/1982 | Satokawa et al. | 568/842 |
| 4,806,694 | 2/1989 | Powell | 568/842 |

*Primary Examiner*—Werren B. Lone
*Attorney, Agent, or Firm*—Connolly and Hutz

[57] ABSTRACT

A process is described for the preparation of fluoroalcohols of the formula below $$R_f\text{—CH}_2\text{—CH}_2\text{—CH—OH}$$
$$|$$
$$R$$

in which $R_f$ is a perfluoroalkyl radical having 1 to 20 carbon atoms and R is hydrogen or an alkyl radical having 1 to 5 carbon atoms, by reaction of a perfluoroalkylethylene, $R_f$—CH=CH$_2$, and an n-C$_1$ to C$_6$-alkanol in the presence of a free radical initiator, the perfluoroalkylethylene, the alkanol and the free radical initiator being used in the molar ratio of 1 to 20–50 to 0.002–0.2. In the novel process, in addition, the reaction is carried out in a specific manner and under specific reaction conditions. The fluoroalcohols given are obtained in high yield.

8 Claims, No Drawings

PROCESS FOR THE PREPARATION OF PRIMARY AND SECONDARY FLUORINE-CONTAINING ALCOHOLS

DESCRIPTION

The invention relates to a process for the preparation of primary and secondary fluorine-containing alcohols of the formula 1 below

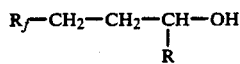

in which $R_f$ is a perfluoroalkyl radical having 1 to 20 carbon atoms, preferably having 6 to 16 carbon atoms, and R is hydrogen (these are primary fluorine-containing alcohols) or an alkyl radical having 1 to 5 carbon atoms (these are secondary fluorine-containing alcohols), by reaction of a perfluoroalkylethylene of the formula 2 below

in which $R_f$ has the meaning given, with an n-$C_1$ to $C_6$-alkanol in the presence of a free radical initiator.

U.S. Pat. No. 3,532,659 discloses primary and secondary fluorine-containing alcohols of the formula below

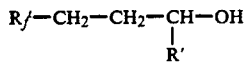

in which $R'_f$ is a perfluoroalkyl radical having 5 to 13 carbon atoms and R' is hydrogen or an alkyl radical having 1 to 5 carbon atoms; compare column 2, reaction equation (c) in connection with column 1, lines 27 to 30, and examples 1 and 17. The primary fluorine-containing alcohols are prepared by reaction of a perfluoroalkylethylene of the formula $R'_f$—CH=$CH_2$ with methanol and the secondary fluorine-containing alcohols by reaction of a perfluoroalkylethylene with an n-$C_2$- to $C_6$-alkanol. The reaction is carried out in the presence of a free radical initiator and with the use of a more or less large excess of alkanol, that is in such a manner that the perfluoroalkylethylene compound, the alcohol and the free radical initiator are mixed together and the mixture is heated to the reaction temperature and is held at this temperature until the completion of the reaction. The preparation, described in the U.S. Pat. No. 3,532,659 mentioned, of the primary and secondary alcohols in question having a perfluoroalkylethylene radical is therefore performed solely in the form of a one-pot process. This procedure leaves something to be desired in particular with regard to yield. Thus the yield in Example 1 is only 80% and in Example 17 actually only 50%.

It has now been found that the reaction of perfluoroalkylethylenes with n-alkanols in the presence of free radical initiators leads to high yields of fluoroalcohols when the perfluoroalkylethylene, the alkanol and the free radical initiator are used in a defined molar ratio and the reaction is carried out in a specific manner.

The process according to the invention therefore comprises using the perfluoroalkylethylene compound, the alkanol compound and the free radical initiator in a molar ratio of 1 to 20–50 to 0.002–0.2, preferably 1 to 25–40 to 0.005–0.1, and carrying out the reaction in such a manner that the alkanol compound is taken first and heated to a temperature which is in the range from 50° C. below to 10° C. above the one-minute halflife temperature of the free radical initiator and is 50° to 230° C., preferably 80° to 200° C., and then at this temperature the perfluoroalkylethylene and the free radical initiator are simultaneously essentially continuously added to the alkanol in a time period of 1 to 10 hours, preferably 2 to 8 hours.

The process according to the invention is therefore based on a combination of essentially three specific characteristics, that is the molar ratio (1) given and the manner given of bringing into contact the perfluoroalkylethylene, alcohol and free radical initiator (2) with maintenance of a defined temperature and metering time (3).

The two reaction components, namely perfluoroalkylethylene and alkanol, and the compound supplying the start radicals are used in a molar ratio of 1 to 20–50 to 0.002–0.2, preferably in the molar ratio of 1 to 25–40 to 0.005–0.1. The alkanol, perfluoroalkylethylene and free radical initiator are brought into contact in such a manner that the two last compounds are simultaneously and within a defined time added to the alkanol compound, which is heated to a defined temperature. The temperature of methanol, ethanol, 1-propanol, 1-butanol, 1-pentanol or 1-hexanol is adjusted to a value which is up to 50° C. below and up to 10° C. above the temperature at which the free radical initiator has a halflife of essentially one minute. A further characteristic of the reaction temperature to be maintained according to the invention is that it should not be below 50° C. and not above 230° C. preferably not below 80° C. and not above 200° C., that is the abovementioned temperature ranges of 50° to 230° C., preferably 80° to 200° C. In the case of the free radical initiator di-tert-butyl peroxide for example, which has a halflife of one minute at 186° C., the alkanol compound is thus heated to a temperature of 186° C.+10° C./−50° C., that is 136° to 196° C.

The perfluoroalkylethylene and the compound forming the start radicals are simultaneously and essentially continuously added to the alkanol compound heated to the stated temperature, in addition a defined time period (metering time) being maintained, that is a time period of 1 to 10 hours, preferably 2 to 8 hours. The simultaneous addition of perfluoroalkylethylene and free radical initiator can for example be carried out in such a manner that the two are mixed together and the mixture is added. The two compounds can also added simultaneously separately from each other, for example from one vessel each. The addition of the perfluoroalkylethylene and the free radical initiator to the alcohol is carried out at a metering rate such that a time period of 1 to 10 hours, preferably 2 to 8 hours, is required. The addition is further carried out essentially continuously, that is uninterruptedly at an essentially constant metering rate or alternatively in portions, but there should not be relatively long intervals of time (at most about 5 minutes) between the individual portions. The addition of perfluoroalkylethylene and free radical initiator will thus lie between dropwise and a more or less gentle flow (in the case of separate addition of the two compounds, the perfluoroalkylethylene to be used in a greater quantity is added at a higher rate than the free radical initiator). After the addition of the perfluoroalkylethylene and the free radical initiator to the alcohol heated to the reaction temperature, the mixture is held for about a further 0.5 to 3 hours at the temperature mentioned for continued reaction. Complete reaction is attained when no or virtually no perfluoroalkylethylene can any longer be detected. The reaction according to the invention is carried out without the use of a separate solvent in an essentially anhydrous medium. The presence of a small quantity of water, that is water up to about 5% by weight, relative to the sum of the weights of perfluoroalkylethylene, alcohol and free radical initiator, generally does not interfere, so that for example industrial methanol, ethanol, n-propanol, n-butanol, n-pentanol and n-hexanol can also be used. Since the boiling point of for example methanol is 65° C. and of ethanol is 78° C., the reaction will generally be carried out under pressure. The reaction can be carried out continuously or discontinuously.

The process according to the invention supplies the target primary and secondary fluorine-containing alcohols in the form of a solution in the alkanol used in excess. Since the reaction to give the target fluoroalcohol proceeds virtually quantitatively and no significant by-products are formed, isolation of the fluoroalcohol from the solution mentioned is often not required at all. If isolation of the fluoroalcohol is desired, the excess alkanol will be separated off simply by distillation. In this case, any organic initiator compound still present is generally also distilled off. The removal of initiator compound can for example also be achieved by washing with water. By means of the process according to the invention the target fluoroalcohols are thus obtained in high yield and high purity.

As far as the starting compounds for the process according to the invention are concerned, the following can be stated:

The perfluoroalkyl group $R_f$ of the perfluoroalkylethylene can be straight or branched, saturated or unsaturated with preferably 1 to 3 double bonds), straight and saturated being preferred. In the case of a branched perfluoroalkyl group, the group with a terminal branch is preferred. The perfluoroalkyl radical frequently relates to a mixture of perfluoroalkyl having the number mentioned of carbon atoms, namely 1 to 20 carbon atoms ($CF_3$ to $C_{20}F_{41}$), preferably 6 to 16 carbon atoms ($C_6F_{13}$ to $C_{16}F_{33}$), or having 6 to 12 carbon atoms ($C_6F_{13}$ to $C_{12}F_{25}$).

Of the n-$C_1$ to $C_6$-alkanols, the first two are preferred, that is methanol and ethanol. As the given molar ratios show, the alkanol compound is used in a great excess.

The free radical initiators used can be inorganic or organic compounds. Generally, those free radical initiators will be chosen which have advantageous halflives and supply active free radicals. Representatives of inorganic free radical initiators which may be mentioned are peroxo acids, peroxoborates, peroxocarbonates, peroxophosphates and peroxodisulfates. Representatives of organic free radical initiators which may be mentioned are the organic peroxides and the azo compounds. Organic free radical initiators are preferred and of these in turn the peroxides, preferably alkyl hydroperoxides, dialkyl peroxides, diacyl peroxides, peroxycarboxylic esters and peroxycarboxylic acids. Organic peroxides are mentioned in detail below, the one-minute halflife temperature being given in brackets: tert-butyl hydroperoxide (179° C.), di-tert-butyl peroxide (186° C.), diacetyl peroxide (122° C.), dilauroyl peroxide (115° C.), dibenzoyl peroxide (133° C.), tert-butyl perpivalate (112° C.) and tert-butyl perbenzoate (163° C.).

As far as the amount of free radical initiator is concerned, this—as described above—is 0.002 to 0.2 mol per mole of perfluoroalkylethylene, preferably 0.005 to 0.1 mol per mole of perfluoroalkylethylene. This depends in particular on the halflife of the free radical initiator and on the activity of the radicals.

The invention is illustrated in still further detail with examples.

EXAMPLE 1

Starting materials:

| | |
|---|---|
| 294.30 g (0.66 mol) | $C_8F_{17}CH=CH_2$ |
| 912.20 g (19.8 mol) | $CH_3CH_2OH$ (anhydrous) |
| 9.65 g (0.066 mol) | di-tert-butyl peroxide |

Molar ratios: 1 to 30 to 0.1.

Procedure:

The ethanol was introduced into an autoclave equipped with stirrer, flushed with nitrogen and heated to 160° C. The perfluorooctylethylene and the peroxide were placed in a receiver and continuously fed from the receiver to the heated ethanol with the aid of a metering pump. The flow rate was set so that the perfluorooctylethylene/peroxide mixture had been added after three hours. The pressure in the autoclave was 13 bar. After the addition, the mixture was maintained for a further two hours at the temperature mentioned for further reaction. To obtain the resulting secondary fluoroalcohol from the reaction mixture, the excess ethanol was distilled off and the bottom product, which represents the secondary fluoroalcohol, was washed repeatedly with water (this work-up of the reaction mixture was also carried out in the further examples, where in the place of water for washing the bottom product, a weakly alkaline aqueous solution was also used).

Result:

The secondary fluoroalcohol $C_8F_{17}CH_2CH_2CH(CH_3)OH$ obtained is a colorless, crystalline waxy product at room temperature. The yield was 95% of theory.

EXAMPLE 2

Starting materials:

| | |
|---|---|
| 294.30 g (0.66 mol) | $C_8F_{17}CH=CH_2$ |
| 845.90 g (26.4 mol) | $CH_3OH$, industrial product |
| 4.82 g (0.033 mol) | di-tert-butyl peroxide |

Molar ratio: 1 to 40 to 0.05.

Procedure:

As in Example 1, with the difference that the introduced methanol was heated to 170° C. The pressure was 21 to 22 bar. After the perfluorooctylethylene/peroxide mixture had been added (metering time 3 hours), the autoclave contents were maintained for a further 1.5 hours at the temperature mentioned for further reaction.

Result:

The primary fluoroalcohol $C_8F_{17}CH_2CH_2CH_2OH$ isolated is a colorless, crystalline waxy product at room temperature. The yield was 93% of theory.

EXAMPLE 3

Starting materials:

| 294.3 g (0.66 mol) | $C_8F_{17}CH=CH_2$ |
|---|---|
| 912.2 g (19.8 mol) | $CH_3CH_2OH$, industrial product |
| 5.8 g (0.033 mol) | tert-butyl perpivalate |

Molar ratio: 1 to 30 to 0.05.
Procedure:
The ethanol was introduced into a reaction vessel equipped with a stirrer, reflux condenser, thermometer and a dropping funnel, flushed with nitrogen and heated to 80° C. The perfluorooctylethylene/peroxide mixture in the dropping funnel was added dropwise in the course of a time period of five hours uninterruptedly to the heated ethanol. After the addition, the mixture was held for a further three hours at 80° C. with stirring for further reaction.
Result:
As in Example 1, with a yield of 93% of theory.

EXAMPLE 4

Starting materials:

| 294.3 g (0.66 mol) | $C_8F_{17}CH=CH_2$ |
|---|---|
| 1,163.6 g (13.2 mol) | n-amyl alcohol (n-pentanol) |
| 11.1 g (0.046 mol) | benzoyl peroxide |

Molar ratio: 1 to 20 to 0.07.
Procedure:
The amyl alcohol was introduced into a reaction vessel equipped with a stirrer, reflux condenser, thermometer and with a dropping funnel and a powder addition funnel, flushed with nitrogen and heated to 105° C. The dropping funnel contained the liquid perfluorooctylethylene and the powder addition funnel the pulverulent benzoyl peroxide. The addition of the perfluorooctylethylene and the benzoyl peroxide from the two addition vessels to the heated amyl alcohol was set so that the two compounds flowed in simultaneously and uninterruptedly in a time period of two hours. After the addition, the mixture was maintained for a further two hours at the given temperature for further reaction.
Result:
The isolated secondary fluoroalcohol

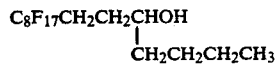

is a colorless, crystalline waxy product at room temperature. The yield was 90% of theory.

EXAMPLE 5

Starting materials:

| 32.4 kg (60.8 mol) | $R_fCH=CH_2$, $R_f=C_6F_{13}$ to $C_{12}F_{25}$ |
|---|---|
| 84.0 kg (1.82 kmol) | ethanol, industrial product |
| 71.6 g (0.49 mol) | di-tert-butyl peroxide |

Molar ratio: 1 to 30 to 0.008.
Procedure:
As in Example 1.
Result:
The secondary fluoroalcohol $R_fCH_2CH_2CH(CH_3)OH$ obtained is a colorless, crystalline waxy product at room temperature. The yield was 93% of theory.

The following comparison examples 1 to 5 are to prove still further the unexpected action of the procedure according to the invention.

COMPARATIVE EXAMPLE 1

Starting materials:

| 294.30 g (0.66 mol) | $C_8F_{17}CH=CH_2$ |
|---|---|
| 912.20 g (19.8 mol) | $CH_3CH_2OH$ (anhydrous) |
| 9.65 g (0.066 mol) | di-tert-butyl peroxide |

Molar ratio: 1 to 30 to 0.1.
Procedure:
The perfluorooctylethylene, the ethanol and the peroxide were introduced into an autoclave equipped with stirrer and flushed with nitrogen. The reaction mixture was heated to 122° C. and was stirred for 24 hours at this temperature. The pressure in the autoclave was 6 bar. To obtain the resulting secondary fluoroalcohol from the reaction mixture, excess ethanol was distilled off and the bottom, product, which represents the secondary fluoroalcohol, was washed repeatedly with water.
Result:
The secondary fluoroalcohol $C_8F_{17}CH_2CH_2CH(CH_3)OH$ obtained is a colorless, crystalline waxy product at room temperature. The yield was 83% of theory.

COMPARISON EXAMPLE 2

Starting materials:

| 294.30 g (0.66 mol) | $C_8F_{17}CH=CH_2$ |
|---|---|
| 912.20 g (19.8 mol) | $CH_3CH_2OH$ (anhydrous) |
| 9.65 g (0.066 mol) | di-tert-butyl peroxide |

Molar ratio: 1 to 30 to 0.1.
Procedure:
The perfluorooctylethylene, the ethanol and the peroxide were introduced into an autoclave equipped with stirrer and flushed with nitrogen. The reaction mixture was heated to 160° C. and was stirred for 24 hours at this temperature. The pressure in the autoclave was around 13 bar. To obtain the resulting secondary fluoroalcohol from the reaction mixture, excess ethanol was distilled off and the bottom product, which represents the secondary fluoroalcohol, was washed repeatedly with water.
Result:
The secondary fluoroalcohol $C_8F_{17}CH_2CH_2CH(CH_3)OH$ obtained is a colorless, crystalline waxy product at room temperature. The yield was 82% of theory.

COMPARISON EXAMPLE 3

Starting materials:

| 294.30 g (0.66 mol) | $C_8F_{17}CH=CH_2$ |
|---|---|
| 912.20 g (19.8 mol) | $CH_3CH_2OH$ (anhydrous) |
| 9.65 g (0.066 mol) | di-tert-butyl peroxide |

Molar ratio: 1 to 30 to 0.1.
Procedure:
The perfluorooctylethylene, the ethanol and the peroxide were introduced into an autoclave equipped with stirrer and flushed with nitrogen. The reaction mixture was heated to 160° C. and was stirred for 5 hours at this temperature. The pressure in the autoclave was around 13 bar. To obtain the resulting secondary fluoroalcohol from the reaction mixture, excess ethanol was distilled off and the bottom product, which represents the secondary fluoroalcohol, was washed repeatedly with water.

Result:
The secondary fluoroalcohol $C_8F_{17}CH_2CH_2CH(CH_3)OH$ obtained is a colorless, crystalline waxy product at room temperature. The yield was 83% of theory.

COMPARATIVE EXAMPLE 4

Starting materials:

| | |
|---|---|
| 89.2 g (0.2 mol) | $C_8F_{17}CH=CH_2$ |
| 114.7 g (3.58 mol) | $CH_3OH$, industrial product |
| 2.92 g (0.02 mol) | di-tert-butyl peroxide |

Molar ratio: 1 to 17.9 to 0.1.

Procedure:
The perfluorooctylethylene, the methanol and the peroxide were introduced into an autoclave equipped with stirrer and flushed with nitrogen. The reaction mixture was heated to 123° C. and was stirred for 17 hours at this temperature. The pressure in the autoclave was around 12 bar. To obtain the resulting primary fluoroalcohol from the reaction mixture, excess methanol was distilled off and the bottom product, which represents the primary fluoroalcohol, was washed repeatedly with water.

Result:
The primary fluoroalcohol $C_8F_{17}CH_2CH_2CH_2OH$ obtained is a colorless, crystalline waxy product at room temperature. The yield was 59% of theory.

COMPARISON EXAMPLE 5

Starting materials:

| | |
|---|---|
| 294.3 g (0.66 mol) | $C_8F_{17}CH=CH_2$ |
| 845.9 g (26.4 mol) | $CH_3OH$, industrial product |
| 4.82 g (0.033 mol) | di-tert-butyl peroxide |

Molar ratio: 1 to 40 to 0.05.

Procedure:
As in Comparison Example 4, with the difference that the reaction mixture was stirred for 4.5 hours at 170° C. The pressure in the autoclave was around 23 bar. To obtain the resulting primary fluoroalcohol from the reaction mixture, excess methanol was distilled off and the bottom product, which represents the primary fluoroalcohol, was washed repeatedly with water.

Result:
The primary fluoroalcohol $C_8F_{17}CH_2CH_2CH_2OH$ obtained is a colorless, crystalline waxy product at room temperature. The yield was 62% of theory.

I claim:
1. A process for the preparation of a primary or secondary fluorine-containing alcohol of the formula 1 below

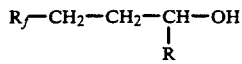

in which $R_f$ is perfluoroalkyl radical having 1 to 20 carbon atoms and R is hydrogen or an alkyl radical having 1 to 5 carbon atoms, by reaction of a perfluoroalkylethylene of the formula 2 below

in which $R_f$ has the meaning given, with an n-$C_6$-alkanol in the presence of a free radical initiator, which comprises using the perfluoroalkylethylene compound, the alkanol compound and the free radical initiator in a molar ratio of 1 to 20–50 to 0.002–0.2, wherein said free radical initiator is selected from the group consisting of dialkyl peroxides, diacyl peroxides and peroxycarboxylic esters and carrying out the reaction in such a manner that the alkanol compound is taken first and heated to a temperature which is in the range from 50° C. below to 10° C. above the one-minute halflife temperature of the free radical initiator and is 50° to 230° C. and then at this temperature the perfluoroalkylethylene and the free radical initiator are simultaneously and essentially continuously added to the alkanol in a time period of 1 to 10 hours.

2. The process as claimed in claim 1, wherein the perfluoroalkylethylene compound, the alkanol compound and the free radical initiator are used in a molar ratio of 1 to 25–40 to 0.005–0.1.

3. The process as claimed in claim 1, wherein the alkanol compound is heated to a temperature which is in the range from 50° C. below to 10° C. above the one-minute halflife temperature of the free radical initiator and is 80° to 200° C.

4. The process as claimed in claim 1, wherein the perfluoroalkylethylene and the free radical initiator are added to the alkanol in a time period of 2 to 8 hours.

5. The process as claimed in claim 1, wherein the perfluoroalkylethylene compound, the alkanol compound and the free radical initiator are used in a molar ratio of 1 to 25–40 to 0.005–0.1 and the reaction is carried out in such a manner that the alkanol compound is taken first and heated to a temperature which is in the range from 50° C. below to 10° C. above the one-minute halflife temperature of the free radical initiator and is 80° to 200° C. and then at this temperature the perfluoroalkylethylene and the free radical initiator are simultaneously and essentially continuously added to the alkanol in a time period of 2 to 8 hours.

6. The process as claimed in claim 1, wherein $R_f$ is a perfluoroalkyl radical having 6 to 16 carbons atoms and R is hydrogen or $CH_3$.

7. The process of claim 1, wherein the free radical initiator tert-butyl hydroperoxide, di-tert-butyl peroxide, diacetyl peroxide, dilauroyl peroxide, dibenzoyl peroxide, tert-butyl perpivalate tert-butyl perbenzoate.

8. The process as claimed in claim 1, wherein the free radical initiator is a di-tert-butyl peroxide or a tert-butyl perpivalate or a benzoyl peroxide.

* * * * *